United States Patent
Weinblatt

(10) Patent No.: US 7,641,341 B2
(45) Date of Patent: Jan. 5, 2010

(54) USE OF SACCADIC EYE MOTION TO INDICATE THE LEVEL OF HUMAN INTEREST IN RESPONSE TO VISUAL STIMULI

(76) Inventor: Lee S. Weinblatt, 465 Winthrop Rd., Teaneck, NJ (US) 07666

( * ) Notice: Subject to any disclaimer, the term of this patent is extended or adjusted under 35 U.S.C. 154(b) by 193 days.

(21) Appl. No.: 11/801,560

(22) Filed: May 10, 2007

(65) Prior Publication Data

US 2007/0273832 A1   Nov. 29, 2007

Related U.S. Application Data

(60) Provisional application No. 60/799,708, filed on May 10, 2006.

(51) Int. Cl.
*A61B 3/14* (2006.01)

(52) U.S. Cl. .................................. 351/210; 351/205

(58) Field of Classification Search .............. 351/210, 351/209, 221, 205, 246; 600/5, 10, 12, 13
See application file for complete search history.

(56) References Cited

U.S. PATENT DOCUMENTS 4,838,681 A * 6/1989 Pavlidis ...................... 351/210
5,632,742 A * 5/1997 Frey et al. ................... 606/12

* cited by examiner

*Primary Examiner*—Hung X Dang
(74) *Attorney, Agent, or Firm*—Cohen, Pontani, Lieberman & Pavane LLP

(57) ABSTRACT

Technique for providing an indication of viewer interest in response to visual stimuli. A viewer is exposed to visual stimuli. The viewer's saccadic eye motion occurring while the viewer is being exposed to the visual stimuli are measured. The visual stimuli are displayed together with the measured saccadic eye motion that occurred while the viewer was being exposed to the visual stimuli as an indication of the viewer's interest in such visual stimuli.

26 Claims, 1 Drawing Sheet

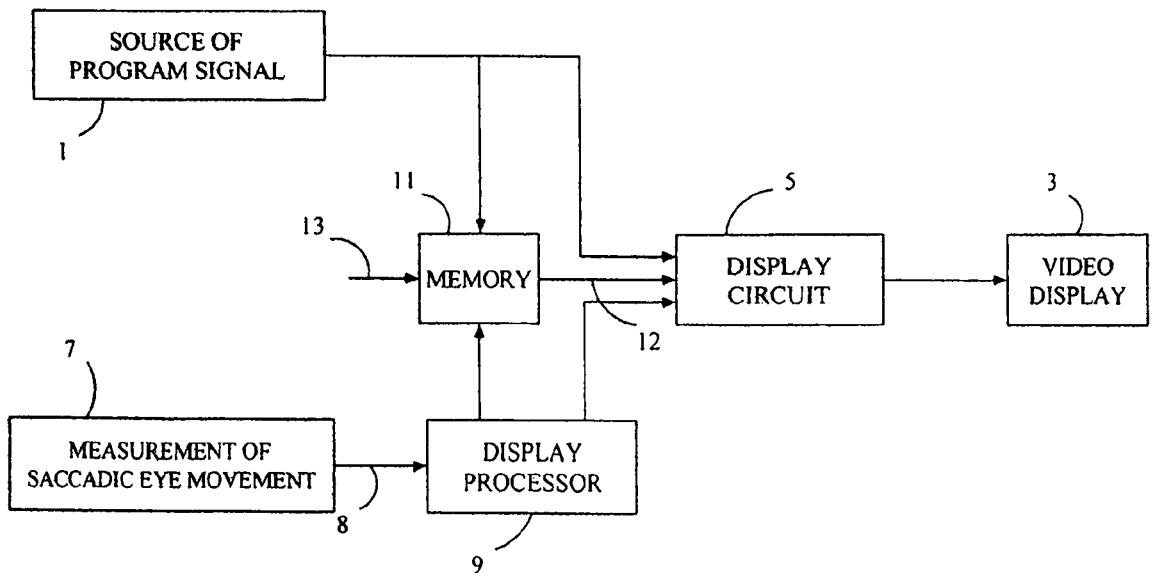

USE OF SACCADIC EYE MOTION TO INDICATE THE LEVEL OF HUMAN INTEREST IN RESPONSE TO VISUAL STIMULI

RELATED APPLICATION

This application claims priority from U.S. Provisional Patent Application Ser. No. 60/799,708 filed on May 10, 2006. The content of which is hereby incorporated herein by reference.

FIELD OF THE INVENTION

The present invention relates to a technique for using eye motion to indicate the level of human interest in response to a given visual stimulus, such as a commercial. In particular, the saccadic eye movements of a viewer exposed to an image are monitored, and a measurement of the viewer's saccadic eye motion is displayed in relation to the image as an indicator of the level of the viewer's visual interest in that image.

BACKGROUND OF THE INVENTION

Apparatus to track eye movement is well known. Such apparatus is available from, for example, ISCAN, Inc. of Burlington, Mass. and Tobii Technology AB of Stockholm, Sweden.

It is known to track eye movement in response to various types of visual stimuli, such as still images, slide shows, movies and the like.

It is also known to use any of a variety of available eye movement monitoring apparatus types, such as stationary eye tracking, head-mounted eye tracking, combined head and eye movement tracking, and so on.

Eye movement tracking has been put to advantageous use in the field of advertising. For example, U.S. Pat. No. 4,075,657 discloses a system for providing a visual indicator of where the viewer is looking and superimposing that indicator on the image then being displayed to the viewer. This enables an analysis of the effectiveness of a commercial by determining whether the viewer's attention is sufficiently attracted to those portions of the commercial which are considered to be of greatest value in selling the advertised product. The content of U.S. Pat. No. 4,075,657 is hereby incorporated by reference in its entirety.

Such an analysis technique is convenient and effective in providing valuable and meaningful results. However, one shortcoming is that it has limitations in determining whether the viewer is bored, highly stimulated, or anything in between while looking at any part of the image. Where along this scale the viewer's level of interest falls is of great interest to an advertiser for the reason that a viewer is more likely to remember a product when the level of interest is high than when it is low.

Up to the present time, determinations of the impact an advertisement makes on consumers have been primarily reliant on telephone surveys. Questions are posed regarding a commercial, for example, but the accuracy and reliability of the responses are inherently suspect because they are subjective and rely on memory of events that happened perhaps some days before.

Consequently, a better indicator which actually measures viewer interest objectively and in real time would be highly valuable to have. However, despite the need for an effective and convenient measurement, and despite the availability of eye movement tracking apparatus and its application to the field of advertising in order to determine where the viewer is looking at any given time, as explained above, up to the present time the usefulness of eye movement tracking in revealing the level of viewer interest in what is being viewed has been of limited value.

It is also well known that visual images, such as in commercials can be made more appealing or less appealing by such factors as pacing, length and accompanying audio. The pacing used, for example, to cut from one scene to another (i.e. it is difficult, and even annoying, to follow if pacing is too fast), the duration of each scene (i.e. viewers can lose interest if it "drags on"), and the copy being read or background music being played (i.e. can enhance the impact of the image or steal attention away from it), can affect the level of viewer interest in terms of the degree of engagement the viewer has with the commercial. Therefore, the input the commercial makes on the viewer in terms of, for example, impression (favorable or unfavorable) and retention (remember or not remember the product). An advertiser seeking to maximize the impact wants to create a high level of viewer interest by suitably adjusting the content of the visual image itself as well as the accompanying elements of the commercial. However, as these factors are "tweaked", some objective and accurate measurement of the results for each set of factors is needed.

SUMMARY OF THE INVENTION

It is an object of the present invention to provide an improved indicator of the level of a viewer's interest in visual stimuli based on a measurement of the viewer's saccadic eye motion.

This and other objects are attained in accordance with one aspect of the invention directed to a method of providing an indication of viewer interest in response to visual stimuli, comprising: exposing a viewer to visual stimuli; monitoring saccadic eye motion of the viewer occurring while the viewer is being exposed to the visual stimuli; and displaying the visual stimuli together with the monitored saccadic eye motion that occurred while the viewer was being exposed to the visual stimuli as an indication of the viewer's interest in such visual stimuli.

Another aspect of the invention is directed to an apparatus for providing an indication of viewer interest in response to visual stimuli, comprising: means for exposing a viewer to visual stimuli; means for monitoring saccadic eye motion of the viewer occurring while the viewer is being exposed to the visual stimuli; and means for displaying the visual stimuli together with the monitored saccadic eye motion that occurred while the viewer was being exposed to the visual stimuli as an indication of the viewer's interest in such visual stimuli.

Other objects and features of the present invention will become apparent from the following detailed description considered in conjunction with the accompanying drawing. It is to be understood, however, that the drawing is designed solely for purposes of illustration and not as a definition of the limits of the invention, for which reference should be made to the appended claims.

BRIEF DESCRIPTION OF THE ONLY DRAWING

The drawing depicts a schematic block diagram of a system for implementing an exemplary embodiment of the invention.

DETAILED DESCRIPTION OF THE ONLY DRAWING

An important contribution of the present invention is the application of saccadic eye movement measurements to provide an indication of viewer interest in the image being viewed. Apparatus to measure saccadic eye motion is available from, for example, the above-mentioned ISCAN, Inc. of Burlington, Mass. and Tobii Technology AB of Stockholm, Sweden.

The definition of a saccade includes fast movement of an eye. The purpose of saccades can be illustrated by referring to the human eye. Humans do not look at a scene in a steady way. Instead, the eyes move around, locating interesting parts of the scene and building up a mental "map" corresponding to the scene. In the human eye, one reason for saccades is that only the central part of the retina, the macula, has a high concentration of color sensitive photoreceptor cells, called cone cells. The rest of the retina is mainly made up of monochrome photoreceptor cells called rod cells, which are especially good for motion detection. Thus, the macula makes up the high-resolution central part of the human retina.

By moving the eye so that small parts of a scene can be sensed with the greater resolution of the macula, body resources can be used efficiently. More specifically, if the entire eyeball were to have a high resolution capability, and if an entire scene were viewed in such high resolution simultaneously, the diameter of the optic nerve would need to be larger than the diameter of the eyeball itself. Subsequent processing of such a high-resolution image would require a brain many times larger than its current size.

The dynamics of saccadic eye motion give insight into the complexity of the mechanism that controls the motion of the eye. The saccade is the fastest movement of an external part of the human body. The peak angular speed of the eye during a saccade reaches up to 1000 degrees per second. Saccades last from about 20 to 200 milliseconds.

In addition to the kind of saccades described above, the human eye is in a constant state of vibration, oscillating back and forth at a rate of about 60 per second. These "microsaccades" are tiny movements, roughly 20 arcseconds in excursion, and are completely imperceptible under normal circumstances. They serve to refresh the image being cast onto the rod cells and cone cells at the back of the eye. Without microsaccades, staring fixedly at something would cause a person's vision to cease after a few seconds since the rods and cones of the human eye only respond to a change in luminance.

An embodiment of the invention will now be described by referring to the only drawing. The viewer is exposed to a visual image provided by a source 1 of program signal. Source 1 can be any type of a visual communication system such as broadcast television, cable television, satellite television, video tape recorder, DVD, delayed presentation such as with Tivo, and so on. The signal from source 1 is directed to video display 3. Display 3 can be any one of the various well known display devices such as a CRT screen, an LCD screen, plasma screen, and so on. A display circuit 5 is used to process the program signal in a well known manner so that it is capable of being properly reproduced by display 3 to be discernible to a human being. Such display circuits are well known and, as such, further details thereof are not deemed necessary.

The program signal being generated by source 1 can be what is commonly known as a commercial, which advertises a product or service, or a performance that is being broadcast by a television network, for example. All of these are commonly referred to herein by the term "program," and the signal which is used for reproducing these on display 3 is referred to herein by the term "program signal".

As the viewer is being shown a program on display 3 based on the signal received from source 1, the viewer's saccadic eye movement is measured by apparatus 7. As explained above, such apparatus is well known and readily available and, thus, details thereof are not deemed necessary. The present invention makes use of saccades, and this is referred to herein as measurement of saccadic eye movement ("MSEM"). Apparatus 7 can provide, inter alia, the number of measured saccades per unit of time, such as per second.

In accordance with the invention, display processor 9 receives the MSEM signal 8 generated by apparatus 7. The display processor 9 converts the MSEM signal 8 to a signal conditioned so as to be capable of being properly reproduced on display 3 in combination with the program, as explained in further detail below.

The output of display processor 9 is inputted to display circuit 5 and also to memory 11. Memory 11 is any one of the well known storage systems used to record an electronic signal. Memory 11 also receives the output from source 1. These two signals are stored in association with each other so that the output of source 1 is, in effect, time synchronized with the output of display processor 9 in the output 12 of memory 11. Consequently, when the MSEM signal data and the program signal data recorded in memory 11 are retrieved to be reproduced on display 3, the result being displayed is a program segment together with the processed version (as explained below) of the MSEM measured simultaneously with that same program segment. Thus, the simultaneous display of the MSEM with the image to which the viewer was reacting provides an indication of the viewer's interest in that image.

Control input signal 13 causes the synchronized MSEM signal data and the program signal data to be retrieved from memory 11 for reproduction on display 3 via display circuit 5. Control input signal 13 can be manually actuated or under some type of automatic control. Of course, as is evident from the only drawing, the MSEM signal and the program signal can also be combined for viewing in real time.

In accordance with an aspect of this invention, the level of viewer interest in a particular image is regarded as being related to the number of saccades, as obtained from MSEM signal 8, that occurs during a given period of time. Thus, an oscillation of 50 per second, just for the sake of illustration, is taken to indicate a higher level of viewer interest than an oscillation of 20 per second. The display processor includes an internal clock (not shown) which can be used to set a selected measurement time period. A reading is obtained of whatever number of oscillations occur during that given time period. Display processor 9 also converts such readings into data suitable for the particular way in which such information is to be displayed. For example, the display could simply be a number superimposed on the program being reproduced on display 3. So, if the number of oscillations per second is 20, the numeral 20 will be displayed at, for example, the bottom right-hand corner of display 3. Alternatively, the display can be a bar graph. The bar graph can include the current reading as well as the previous, say, 10 readings. In this way, it is possible to view and assess the trend in the viewer's level of interest whether it is stable, dropping or rising. Of course, various other kinds of displays will readily occur to anyone with ordinary skill in the art.

Up to this point, it has been assumed that the visual display from the MSEM apparatus being shown on display 3 is that of a single individual. However, this is not necessarily the case.

It is also possible to display the average of readings from a plurality of viewers reacting to that particular image. In such a case, input signal 13 will trigger memory 11 to output the data for a plurality of viewers, including the current one, synchronized with the particular signal then being received from source 1.

Of course, it is readily apparent that the visual indicator that is being shown on display 3 can be the actual reading of the oscillations, it can be the actual reading divided by a given number or multiplied by a given number. This depends in part on design preferences and in part on the characteristics and requirements of the various components that are involved. Of course, the indicator can also be an audio tone or message.

The term "image" as used herein is applied to the entire screen of display 3 or it can apply to the particular portion of the screen being actually looked at by the viewer. Display 3 can also show an indicator, such as a cursor, superimposed in real time on the portion of the display being looked at by the viewer.

Although the description provided above has discussed measuring saccades, it is also useful to measure the microsaccades and to apply that measurement along with or instead of the measurement of saccades.

Thus, this invention provides the MSEM on display 3 as an indicator of viewer interest which is superimposed on the image which provided the visual stimulus to the viewer. Such a presentation provides a unique measurement that effectively reveals the level of viewer interest based on the number of MSEM oscillations occurring in response to the visual stimulus being displayed to the viewer.

To summarize, referring to the drawing, saccadic eye motion is used to indicate a level of human interest in response to visual stimuli comprises exposing a viewer to an image provided as a visual stimulus by a program signal source 1. More specifically, the saccadic eye motion of the viewer is measured by apparatus 7 while the viewer is being exposed to the image displayed from the program signal. The measured saccadic eye motion of the viewer that is generated by apparatus 7 is provided to the display processor 9. The measured saccadic eye motion of the viewer is then converted by the display processor 9 into a signal conditioned for reproduction on the display 3 together with the visual stimuli provided from the program signal. The output of display processor 9 is inputted to display circuit 5 and also to memory 11. In addition, memory 11 receives the output from the program source 1. These two signals are stored in association with each other so that the output of program source 1 is, in effect, synchronized with the output of display processor 9 in the output 12 of memory 11. The level of the viewer's saccadic eye motion is determined. Although not shown, the display processor 9 includes an internal clock that can be used to set the predetermined amount of time in which to perform the measurement. An indication of the level of human interest in response to the visual stimulus is provided based on the saccadic eye motion of the viewer displayed in juxtaposition with the associated program segment to which the viewer was reacting.

Although the description provided above discusses details of embodiments of the invention, it is clear that various changes and alternatives thereto would readily occur to a person with ordinary skill in the art. All such changes are intended to fall within the scope of the present invention as defined by the following claims.

I claim:

1. A method of providing and indication of viewer interest in response to visual stimuli, comprising:
    exposing a viewer to visual stimuli;
    monitoring saccadic eye motion of the viewer occurring while the viewer is being exposed to the visual stimuli; and
    displaying the visual stimuli together with the monitored saccadic eye motion that occurred while the viewer was being exposed to the visual stimuli as an indication of the viewer's interest in such visual stimuli.

2. The method of claim 1, wherein the step of monitoring saccadic eye motion of the viewer comprises measuring microsaccadic eye motion.

3. The method of claim 1, wherein the step of monitoring saccadic eye motion comprises measuring the number of saccadic eye movements occurring during a designated period of time.

4. The method of claim 3, wherein the number of saccadic eye movements occurring during a designated period of time is a number of oscillations per second.

5. The method of claim 4, wherein a higher number of oscillations per second is displayed as an indication of a higher level of viewer interest.

6. The method of claim 4, further comprising the step of:
    obtaining a reading of the number of oscillations that occur during the predetermined time period; and
    converting the readings into data suitable for display.

7. The method of claim 6, wherein the reading is converted into a number superimposed on a program being reproduced on a display.

8. The method of claim 6, wherein the reading is converted into a bar graph superimposed on a program being reproduced on a display.

9. The method of claim 8, wherein the bar graph includes a current reading and at least one previous reading to provide an indication of a trend.

10. The method of claim 6, wherein the reading of the number of oscillations comprises an average of the saccadic eye motion of a plurality of viewers reacting to the visual stimuli.

11. The method of claim 3, wherein the displaying step displays the visual stimuli together with an average of the saccadic eye movements of a plurality of viewers reacting to the same visual stimuli.

12. The method of claim 1, wherein the visual stimuli are from a commercial or a performance that is being broadcast by a television network.

13. The method of claim 1, further comprising the steps of:
    storing in a memory data corresponding to a program signal used for generating the visual stimuli to which the viewer was exposed;
    storing in the memory data corresponding to the measured saccadic eye motion of the viewer occurring while the viewer was being exposed to the visual stimuli; and
    retrieving from the memory program signal data corresponding to visual stimuli and, in association therewith for simultaneous display, data corresponding to the measured saccadic eye motion of the viewer that occurred while the viewer was being exposed to the visual stimuli related to the retrieved program signal data.

14. Apparatus for providing an indication of viewer interest in response to visual stimuli, comprising:
    means for exposing a viewer to visual stimuli;
    means for monitoring saccadic eye motion of the viewer occurring while the viewer is being exposed to the visual stimuli; and
    means for displaying the visual stimuli together with the monitored saccadic eye motion that occurred while the viewer was being exposed to the visual stimuli as an indication of the viewer's interest in such visual stimuli.

15. The apparatus of claim 14, wherein the means for monitoring saccadic eye motion of the viewer comprises means for measuring microsaccadic eye motion.

16. The apparatus of claim 14, wherein the means for monitoring saccadic eye motion comprises means for measuring the number of saccadic eye movements occurring during a designated period of time.

17. The apparatus of claim 16, wherein the number of saccadic eye movements occurring during a designated period of time is a number of oscillations per second.

18. The apparatus of claim 17, wherein a higher number of oscillations per second is displayed as an indication of a higher level of viewer interest.

19. The apparatus of claim 17, further comprising:
means for obtaining a reading of the number of oscillations that occur during the predetermined time period; and
means for converting the readings into data suitable for display.

20. The apparatus of claim 19, wherein the means for converting converts the readings into a number superimposed on a program being reproduced on the means for displaying.

21. The apparatus of claim 19, wherein the means for converting converts the readings into a bar graph superimposed on a program being reproduced on the means for displaying.

22. The apparatus of claim 21, wherein the bar graph includes a current reading and at least one previous reading to provide an indication of a trend.

23. The apparatus of claim 19, wherein the means for obtaining a reading of the number of oscillations comprises means for obtaining an average of the saccadic eye motion of a plurality of viewers reacting to the visual stimuli.

24. The apparatus of claim 16, wherein the means for displaying displays the visual stimuli together with an average of the saccadic eye movements of a plurality of viewers reacting to the same visual stimuli.

25. The apparatus of claim 14, wherein the visual stimuli are from a commercial or a performance that is being broadcast by a television network.

26. The apparatus of claim 14, further comprising:
means for storing in a memory data corresponding to a program signal used for generating the visual stimuli to which the viewer was exposed;
means for storing in the memory data corresponding to the measured saccadic eye motion of the viewer occurring while the viewer was being exposed to the visual stimuli; and
means for retrieving from the memory program signal data corresponding to visual stimuli and, in association therewith for simultaneous display, data corresponding to the measured saccadic eye motion of the viewer that occurred while the viewer was being exposed to the visual stimuli related to the retrieved program signal data.

* * * * *